United States Patent
Zhao et al.

(10) Patent No.: US 11,909,047 B2
(45) Date of Patent: Feb. 20, 2024

(54) OLIGOMER OF N,N'-DI(HETERO)ARYL-5,10-DIHYDROPHENAZINE, CATHODE ACTIVE MATERIAL, CATHODE, BATTERY THEREOF, AND PROCESS FOR PREPARING SAME

(71) Applicant: SOOCHOW UNIVERSITY, Suzhou (CN)

(72) Inventors: Yu Zhao, Suzhou (CN); Gaole Dai, Suzhou (CN); Yumin Qian, Suzhou (CN); Xiaohong Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 805 days.

(21) Appl. No.: 16/971,646

(22) PCT Filed: May 18, 2018

(86) PCT No.: PCT/CN2018/087501
§ 371 (c)(1),
(2) Date: Aug. 20, 2020

(87) PCT Pub. No.: WO2019/218347
PCT Pub. Date: Nov. 21, 2019

(65) Prior Publication Data
US 2020/0388847 A1    Dec. 10, 2020

(51) Int. Cl.
| | | |
|---|---|---|
| H01M 4/60 | (2006.01) | |
| C07D 403/14 | (2006.01) | |
| H01M 10/0525 | (2010.01) | |
| H01M 10/054 | (2010.01) | |
| H01M 4/02 | (2006.01) | |

(52) U.S. Cl.
CPC .......... *H01M 4/608* (2013.01); *C07D 403/14* (2013.01); *H01M 10/054* (2013.01); *H01M 10/0525* (2013.01); *H01M 2004/028* (2013.01)

(58) Field of Classification Search
CPC ..................................................... H01M 4/608
See application file for complete search history.

(56) References Cited

FOREIGN PATENT DOCUMENTS

| | | |
|---|---|---|
| DE | 4325591 A1 | 2/1995 |
| JP | 2011113839 A | 6/2011 |
| WO | 2014189122 A1 | 11/2014 |

OTHER PUBLICATIONS

Muench, S.; Wild, A.; Friebe, C.; Haupler, B.; Janoschka, T.; Schubert, U. S. Chem. Rev. 2016, 116, 9438.*
Goodson "Palladium-Catalyzed Synthesis of Pure, Regiodefined Polymeric Triarylamines" J. Am. Chem. Soc. 1999, 121, 7527-7539.*
Lee, Minah "Multi-electron redox phenazine for ready-to-charge organic batteries." Green Chemistry, 2017, 19(13), 2980-2985.*
Tran Van, Francois et al., "Polyethyleneoxide-dihydrophenazine block copolymer as a cathode material for lithium-polymer batteries" Electrochimica Acta, vol. 43, No. 14, Dec. 31, 1998.

* cited by examiner

*Primary Examiner* — David K O'Dell
(74) *Attorney, Agent, or Firm* — SZDC Law PC

(57) ABSTRACT

The present invention relates to an oligomer-based organic battery materials, cathode active material, cathode and secondary battery comprising such material, and a process for preparing such materials.

3 Claims, 7 Drawing Sheets

1a

1b

1c

OLIGOMER OF N,N'-DI(HETERO)ARYL-5,10-DIHYDRO-PHENAZINE, CATHODE ACTIVE MATERIAL, CATHODE, BATTERY THEREOF, AND PROCESS FOR PREPARING SAME

The present application is the national phase of International Application No. PCT/CN2018/087501, titled "OLIGOMER OF N,N'-DI(HETERO)ARYL-5,10-DIHYDRO-PHENAZINE, CATHODE ACTIVE MATERIAL, CATHODE, BATTERY COMPRISING THE OLIGOMER, AND PROCESS FOR PREPARING THE SAME", filed on May 18, 2018, which is incorporated herein by reference

FIELD

The present invention relates to the secondary battery field and particularly relates to polymer-based organic battery materials and their related applications in batteries.

BACKGROUND

Electrical energy storage systems play a critical role in enabling utilization of electricity generated from intermittent renewable energy sources, and impact profoundly the renewable energy future of a sustainable society. Take lithium-ion battery as an example, in addition to the capacity, the cell voltage and the charge/discharge performance of state-of-the-art battery systems, safety, cost, weight, sustainability and environmental friendliness are important properties of charge storage systems. In particular, the ever growing market for small and thin mobile devices requires small, thin, and lightweight battery systems that also need to be flexible for some applications.

However, the fabrication of these energy storage systems reaches the limits of the lithium-ion battery technologies, which are based on hard electrode materials such as meal oxide nanoparticles or nanocoatings for cathode materials and lithium foils or nanocarbon materials for the anodes. Organic electrode materials, in particular polymers, display an inherent advantage, e.g., they are flexible and their redox properties can be tailored in a straightforward way by adjusting the structure using organic synthesis approaches and are being extensively researched recently. More interestingly, most of these organic are electroactive, not only towards lithium but in principle any metal, because their redox mechanism is based on conversion reactions. Therefore, it is promising that organic materials applied in lithium-ion batteries could be successfully extended to sodium, magnesium, zinc and air-batteries.

But, the reversibility of many polymer-based organic battery materials is limited, owing to the dissolution in organic electrolyte and chemical bond cleavage/recombination during lithiation/delithiation. The former causes internal shuttle thus lowering the efficiency of the cell, while the latter is very likely to bring in undesired side reaction that seriously shortens the cyclability of the cell. Moreover, other adverse factors such as low thermal stability and/or large voltage hysteresis also remain problematic.

It was noted that among the phenazines, N,N'-substituted phenazine derivatives are of particular interest. These molecules undergo two successive one-electron transfer reactions (see FIG. 1a), thus can be categorized as p-type molecules, which usually show higher redox potential than the n-type ones.

SUMMARY

The inventors of the present invention have made attempts to manipulate the conjugation of phenazine derivatives and surprisingly found that an oligomer of phenazine derivatives as shown in the following formula (I) can be suitably used as a high-voltage organic battery cathode material.

Formula (I)

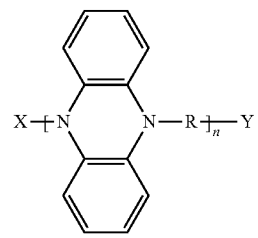

wherein X is same or different, H or substituted or unsubstituted aryl or heteroaryl; Y is H or

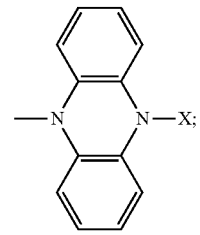

R is substituted or unsubstituted arylene or heteroarylene; and n is from 3 to 30, preferably 4 to 20, more preferably 6 to 10 and still more preferably 8 to 9.

The redox active electron localized on the dihydrophenazine unit in this oligomer is believed to contribute to the good electrochemical performances.

The present invention also provides an oligomer mixture comprising two or more oligomer as recited above.

In another aspect of the invention, it is provided a process for preparing the above oligomer mixture, which comprises the following steps:
1) reacting 5,10-dihydrophenazine with hal-R-hal;
2) optionally, adding X'-hal for endcapping; and/or
3) optionally, adding Y'—H for further endcapping;
wherein hal represents halogen atom, such as Cl, Br, I, X' is same or different substituted or unsubstituted aryl or heteroaryl; Y' is

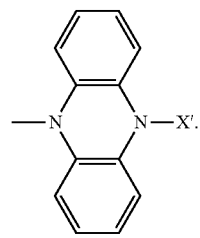

Also, it is provided a process for preparing the oligomer of formula (I), comprising further isolating the oligomer from the above recited oligomer mixture or the oligomer mixture prepared by the above process. Preferably, the isolation is to purify by Physical Vapor Deposition instrument.

In a further aspect of the invention, the present invention provides a cathode active material comprising an oligomer of the above formula (I) or an oligomer mixture thereof; a cathode and a battery comprising the above cathode active material. Preferably, the battery can be selected from the group consisting of Li-ion battery, Na-based battery and Mg-based battery and so on.

In a still further aspect of the invention, the invention provides the use of an oligomer of the above formula (I) or an oligomer mixture thereof for the preparation of cathode active material.

In addition, the present invention provides the use of monomeric N,N-diphenyl-5,10-dihyfrophenazine (briefed as DPPZ and shown below) for preparing cathode active material as well.

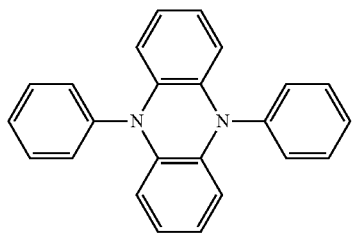 [SMILES: c1ccc(N2c3ccccc3N(c3ccccc3)c3ccccc32)cc1]

BRIEF DESCRIPTION OF DRAWINGS

FIG. 7 shows electrochemical performance of p-DPPZ Li cell, wherein FIG. 7a shows charge/discharge profile, FIG. 7b shows corresponding specific charge/discharge capacity (Cs), Coulombic efficiency (CE) and energy efficiency (EE) with current rate of 1/4 C (upper panel) and 1 C (lower panel) for 500 cycles, FIG. 7c shows power performance with current rate of 1/2, 1, 2 and 5 C and FIG. 7d shows a comparison of discharge voltage, specific capacity and energy density distribution of p-DPPZ with other organic materials for Li-ion batteries.

FIG. 8 shows redox behaviour of DPPZ, wherein FIG. 8a shows CV profiles of DPPZ recorded at a sweeping rate of 10 mV s$^{-1}$ for 100 cycles, FIG. 8b shows RDE profiles upon DPPZ oxidation on a glassy carbon electrode at a sweeping rate of 10 mV s$^{-1}$ with 7 rotation speed of 2500, 3025, 3600, 4225, 4900, 5625 and 6400 rpm. FIG. 8c shows Levich plots of limiting current ($i_{lim}$) versus the square root of rotation speed ($\omega^{1/2}$) and FIG. 8d shows overpotential ($\eta$) dependent current density as a function of $\omega^{-1/2}$ derived from the RDE profiles. 8 overpotentials of 5, 10, 15, 20, 30, 40, 60 and 80 mV are used. FIG. 8e shows $\eta$ as a function of the logarithm of kinetic current ($i_K$).

DETAILED DESCRIPTION OF THE INVENTION

The present inventor surprisingly found that if the substituted groups which connected to the two N atoms on phenazines are chosen as R in formula (I),

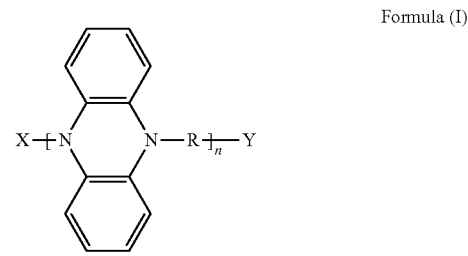

Formula (I)

R being substituted or unsubstituted arylene or heteroarylene, preferably, substituted or unsubstituted arylene or heteroarylene with 6 to 20 carbon atoms, the aromaticity of dihydrophenazine unit could be enhanced by keeping the phenazine-ring in plane and benefits for retaining the molecular stability In the context of the present invention, the term "arylene" refers to a group wherein a hydrogen atom is removed from an "aryl" group. As generally known in the organic filed, the "aryl" group denotes an aromatic carbocyclic group, consisting of a single ring or multiple rings either condensed or linked by a covalent bond such as, but not limited to, phenyl, naphthyl, phenanthryl, and biphenyl. In addition, the "aryl" group may be substituted by any known substituent. The aryl may be substituted by any suitable groups, such as, but not limited to, one or more substituents each independently selected from for example, halogen, S, —OR$_1$, —COR$_1$, —COOR$_1$, —OCOOR$_1$, —CN, —SR$_1$, —(C1-C8)alkyl, —O—(C1-C8)alkyl, wherein R$_1$ each independently is H, (C1-C6)alkyl, or aryl.

In the context of the present invention, the term "heteroarylene" refers to a group wherein a hydrogen atom is removed from a "heteroaryl" group. As generally known in the organic field, an "heteroaryl" group denotes an aromatic carbocyclic group, radical derived from a mono- or polycyclic heteroaromatic ring containing one or three, preferably 1-2, heteroatoms selected from the group consisting of N, O and S. When the heteroaryl is a monocyclic ring, it is preferably a radical of a 5-6-membered ring such as, but not limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-thiazinyl, 1,3,4-thiazinyl, and 1,3,5-thiazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-c]pyridyl, benzimidazolyl, benzthiazolyl, benzoxazolyl, pyrido[1,2-α]pyrimidinyl and 1,3-benzodioxinyl.

In addition, the heteroaryl may be substituted by any suitable groups, such as, but not limited to, one or more substituents each independently selected from halogen, S, —OR$_1$, —COR$_1$, —COOR$_1$, —OCOOR$_1$, —CN, —SR$_1$, —(C1-C8)alkyl, —O—(C1-C8)alkyl, wherein R$_1$ each independently is H, (C1-C6)alkyl, or aryl. It is to be understood that when a polycyclic heteroaryl is substituted, the substitution may be in any of the carbocyclic and/or heterocyclic rings.

Figure 1:
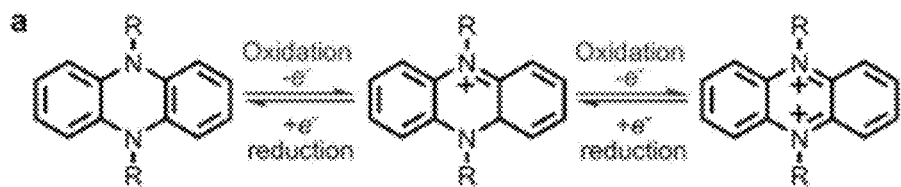
FIG. 1a shows chemical structure and redox mechanism of N,N-substituted phenazine derivatives.
FIG. 1b shows the substitution of phenyl, methyl, vinyl and ethynyl on the N atoms of dihydrophenazine.
FIG. 1c is schematic demonstration of the optimized molecular geometry of N,N-substituted phenazine derivatives.
Figure 1:
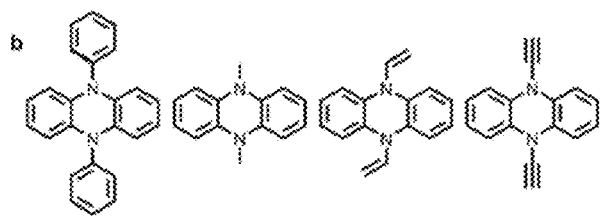
Figure 1:
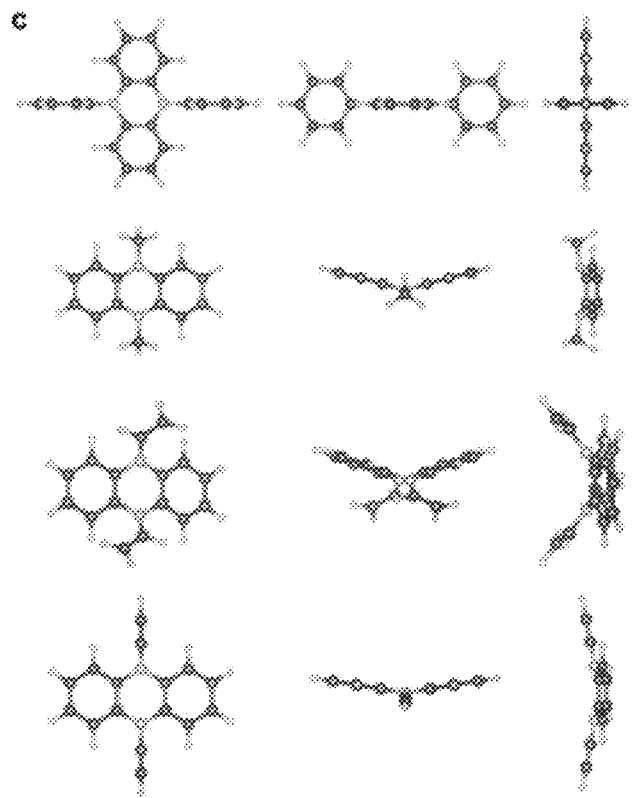

Not wishing to be bound by theory, the present inventors have compared different kinds groups of phenyl, methyl, vinyl and ethynyl (see FIG. 1b) as substituted group on the N atoms of dihydrophenazine in this regard.

By comparison, it has been discovered and concluded that when the substituted group on the N atoms of dihydrophenazine is aryl or heteroaryl such as phenyl, the aromaticity of dihydrophenazine unit could be enhanced by keeping the skeleton in plane, which benefits for retaining the molecular stability. In contrast, when methyl, vinyl and ethynyl are respectively used as the substituted group, the optimized structure of dihydrophenazine unit is distorted (see FIG. 1c), which may lead to decreased aromaticity. The decrease in aromaticity would result in the localization of electrons during the redox process and decreases the molecular stability.

Further, density functional theory (DFT) calculations are used to investigate the electronic structure change during the oxidation reaction of oligomer of N,N-diphenyl-5,10-dihydrophenazine (p-DPPZ), the structure thereof is shown below:

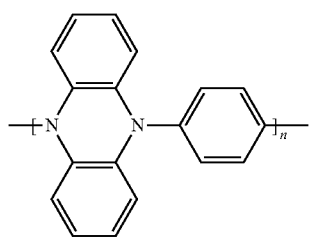

Figure 2:
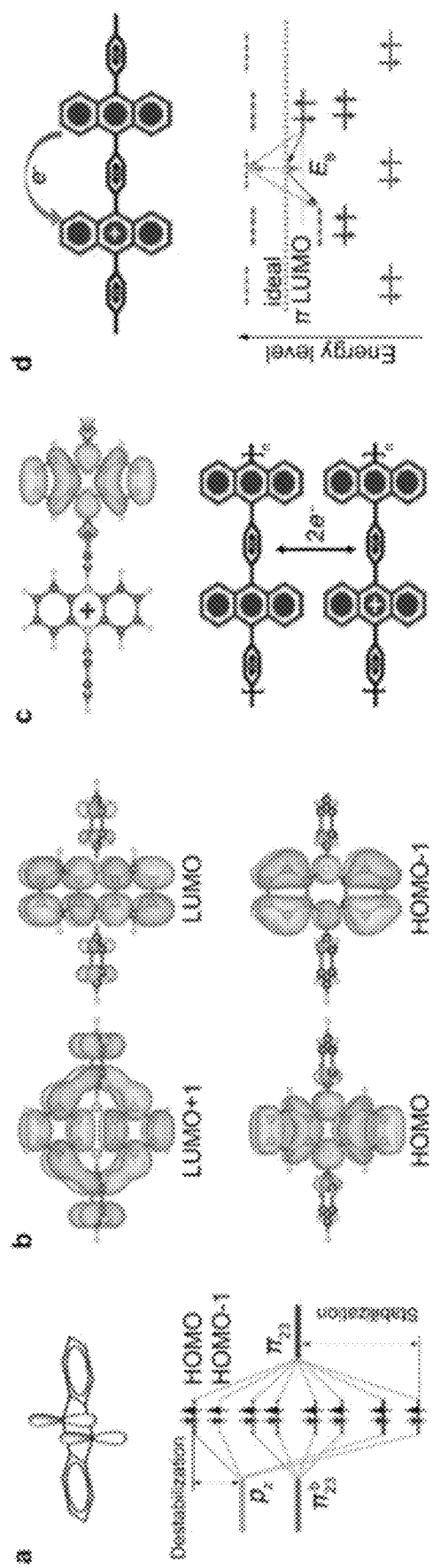
FIG. 2a shows π-LP-π bonding geometry, wherein the upper panel depicts the N 2p lone pair (LP) electron and the π orbital of the neighbouring aromatic ring, and the lower panel depicts the bonding of the N 2p orbital and π orbital of the aromatic ring. $\pi_{23}^b$ and $\pi_{23}$ are the orbitals from the benzene bridge and three aromatic rings, respectively.
FIG. 2b is HOMO and LUMO profiles of a oligomer of N,N-diphenyl-5,10-dihydrophenazine (briefed as p-DPPZ hereinafter) unit.
FIG. 2c is calculated HOMO of p-DPPZ in the charged state (upper panel) and the schematically illustration of the donor-cation-donor chain during the charging/discharging process.
FIG. 2d shows electron transfer dynamics between adjacent p-DPPZ units, the "+" sign stands for the positively charged p-DPPZ unit and $E_B$ is the kinetic barrier for the electron transfer.

DFT calculations show that as seen from the upper panel of FIG. 2a, the extra two 2p$_z$ lone pair (LP) orbitals on the N atoms and π orbitals of its neighbouring aromatic ring lies perpendicular and parallel to the plane of the three-aromatic ring respectively. The π orbital of the aromatic ring is composed of C-2p$_z$ orbitals, which are able to form weak π bond with N-2p$_z$ orbitals even though the orthogonal arrangement between the N-2p$_z$ orbitals and π orbital as shown in the lower panel of FIG. 2a.

The π-LP-π bonding can be formed along three aromatic ring that further stabilizes the structure. There are also very weak σ bonding between the benzene connector $π_{23}^b$ and $π_{23}$ due to the weak orthogonal overlap. Four electrons from the aromatic ring occupy the bonding orbital, while the two N-2p$_z$ orbital electrons occupy the anti-bonding orbitals. However, the degenerate π ($π_2$ and $π_3$) orbital have the same energy with different symmetry. Their bonding with the N-2p$_z$ orbitals causes the week splitting of the degeneracy to form the HOMO of DPPZ.

From the shape and phase of the HOMO and HOMO-1 profiles of p-DPPZ shown in FIG. 2b, the HOMO should be the π anti-bond orbital. Upon charging, two electrons from HOMO are depleted from each N atom. The removal of antibonding electrons can enhance the stability of the structure, which leading to the slight structure variation by means of bond length contraction and elongation. The patterns of bond length change correspond well to the π-LP-π bonding mode of HOMO. The remaining two electrons from N 2p orbitals keep the π-LP-π bonding intact as shown in the upper panel of FIG. 2c. Such π bonding configuration keeps DPPZ stable both in charged and discharged states. Moreover, the HOMO is mainly localized in the three-aromatic ring, so the oligomer would benefit from such localized electron structure, which is free of interaction between active unit, to achieve good voltage profile and high density of active sites. Indeed, p-DPPZ forms donor-acceptor-donor chain and cation-acceptor-cation chain structure in natural and charged state, respectively, as shown in the lower panel of FIG. 2c. Such structures relief the strong charge-charge interaction makes the p-DPPZ maintaining high stability during the charge/discharge process.

Besides, the electron transfer kinetics can benefit from such chain structure. The kinetic barrier for electron transfer can be sophisticated by replacing benzene unit with other functional group with a lower LUMO level close to the ideal LUMO level (FIG. 2d). With such structural tuning, it's possible for the oligomer to exhibits higher electrical conductivity, which is beneficial for fast charging capability and reducing the inactive carbon content of the electrode, thus further enhancing the power and energy density.

Accordingly, the present inventors accomplished the invention by finding out that an oligomer of phenazine derivatives as shown in formula (I) or a mixture thereof is suitably used as a high-voltage organic battery cathode material,

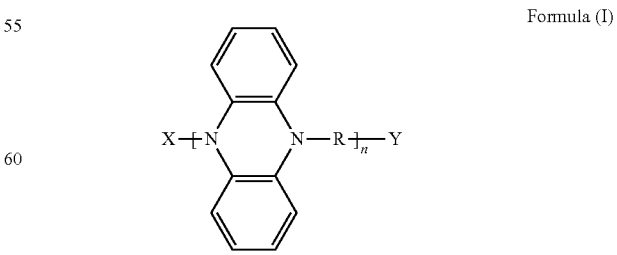

Formula (I)

wherein X is same or different, H or substituted or unsubstituted aryl or heteroaryl; Y is H or

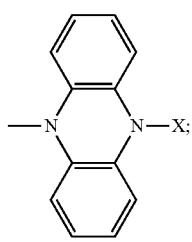

R is substituted or unsubstituted arylene or heteroarylene; and n is from 3 to 30.

In a preferred embodiment of the present invention, R in formula (I) is substituted or unsubstituted m-, or p-phenylene, more preferably, R in formula (I) is p-phenylene.

In a further preferred embodiment of the present invention, X in formula (I) is same or different H or phenyl, and Y in formula (I) is H,

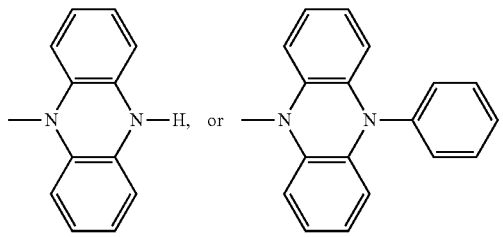

R is p-phenylene.

In a still further preferred embodiment of the present invention, X in formula (I) is same or different H or phenyl, and Y in formula (I) is H,

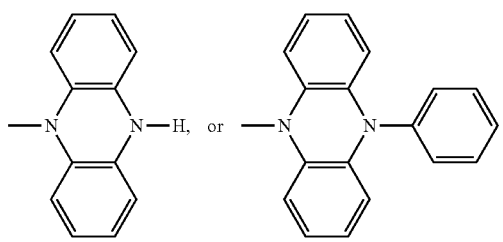

R is p-phenylene, and n is 8 and/or 9.

The present invention also provides an oligomer mixture comprising two or more oligomer of the above formula (I) which can be also used as cathode active material. In the context of the present invention, "an oligomer mixture" may comprise two, or three, or fore, or five, or more oligomers of the formula (I) wherein n is any integer selected from the range of 3 to 30, for example, n can be selected from the group consisting of 3, 4, 5, 6, 7, 8, 9, 10, 11, 12, and 13, and so on.

Preferably, an oligomer mixture comprises two or more oligomers of the formula (I) wherein n is 4 to 20, more preferably 6 to 10 and still more preferably 8 to 9 is provided.

In a preferable embodiment, an oligomer mixture comprises two oligomers of the formula (I) wherein n is 4, 5 respectively, or an oligomer mixture comprises two oligomers of the formula (I) wherein n is 8, 9 respectively and an oligomer mixture comprises two oligomers of the formula (I) wherein n is 11, 12 respectively.

As for the process for preparing the above oligomer mixture, it comprises the following steps:
1) reacting 5,10-dihydrophenazine and hal-R-hal;
2) optionally, adding X'-hal for endcapping; and/or
3) optionally, adding Y'—H for further endcapping;
wherein hal represents halogen atom, such as Cl, Br or I, X' is same or different substituted or unsubstituted aryl or heteroaryl; Y' is

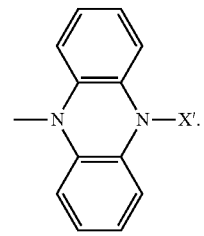

The steps 2) and 3) are not necessary. In some situations, both steps 2) and 3) are omitted and in other situations, either step 2) or 3) is omitted. In the situation wherein both steps 2) and 3) are performed, the sequence of step 2) and 3) is not particularly limited, either step 2) or step 3) can be performed prior to the other step.

In a preferred embodiment of the present invention, 5,10-dihydrophenazine is reacted with 1,4-dibromobenzene in the presence of Pd-containing catalyst (such as $Pd(OAc)_2$). The temperature and reacting time can be suitably adjusted depending on the intended polymerization degree. Optionally, 5-phenyl-5,10-dihydrophenazine solution was added for end capping. And, optionally, bromobenzene was added into reaction mixture for end capping. The time period for endcapping can be suitably adjusted in accordance with the desired products.

Also, it is provided a process for preparing the oligomer of formula (I), comprising further isolating the oligomer from the oligomer mixture prepared by the above process. Preferably, the isolation is to purify by Physical Vapor Deposition instrument.

In a further aspect of the invention, the present invention provides a cathode active material comprising an oligomer of the above formula (I) or an oligomer mixture thereof; a cathode and a battery comprising the above cathode active material. Preferably, the battery can be selected from the group consisting of Li-ion battery, Na-based battery and Mg-based battery and so on.

In a still further aspect of the invention, the invention provides the use of an oligomer of the above formula (I) or an oligomer mixture thereof for the preparation of cathode active material.

EXAMPLES

The following non-limiting examples illustrate various features and characteristics of the present invention, the scope of the present invention should not to be construed as limited thereto:

The preparation of p-DPPZ

All reagents were purchased from commercial sources without further purification.

Anhydrous toluene and o-xylene were distilled from sodium-benzophenone immediately prior to use. 5,10-dihydrophenazine and 5-phenyl-5,10-dihydrophenazine were prepared according to Yang, L., Li, X., Yang, J., Qu Y. & Hua, J. Colorimetric and ratiometric near-infrared fluorescent cyanide chemodosimeter based on phenazine derivatives. ACS Appl. Mater. Inter. 5, 1317-1326 (2013) and Terada, E., Okamoto, T., Kozaki, M., Masaki, M. E., Shiomi, D., Sato, K., Takui, T. & Okada, K. Exchange Interaction of 5,5'-(m- and p-Phenylene) bis(10-phenyl-5,10-dihydrophenazine) Dications and Related Analogues. J. Org. Chem. 70, 10073-10081 (2005).

A mixture of monomer 5,10-dihydrophenazine (273 mg, 1.5 mmol), monomer 1,4-dibromobenzene (354 mg, 1.5 mmol), catalyst Pd(OAc)$_2$ (20 mg, 6 mol %), ligand XPhos (86 mg, 12 mol %) and tBuONa (288 mg, 3 mmol) in anhydrous o-xylene (20 mL) was degassed by three freeze-pump-thaw cycles. The mixture was stirred at 110° C. for 24 hrs and 145° C. for another 24 hrs under argon.

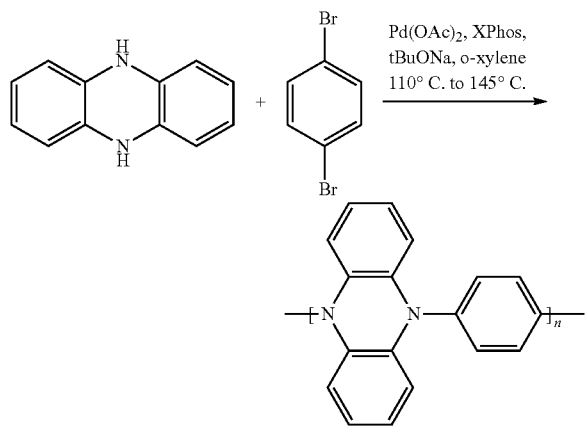

Then the as-prepared 5-phenyl-5,10-dihydrophenazine solution (4 mL, 1 mmol) was added into reaction mixture for end capping. After cooling to room temperature, the mixture was filtered. The solid part (crude product) was washed with large amount of hot o-xylene, dichloromethane (DCM), MeOH and H$_2$O. The solubility of the p-DPPZ is very poor. Thus, the product was dispersed in DCM by mortar and ultrasonic wave, then filtered and washed by DCM, THF, Et$_3$N, MeOH and H$_2$O. This procedure was repeated for five times to give the purer product p-DPPZ. Then the product was purified by Physical Vapor Deposition (PVD) instrument under 350° C. and vacuum for 12 hours to remove small molecule weight products. Finally, the final product p-DPPZ was obtained as a brownish black solid (281 mg) in 73% yield. MALDI-TOF Mass H(C$_{18}$H$_{12}$N$_2$)$_n$H: 2048.704 (n≈8), 2305.800 (n≈9); Elemental Analysis: calculated for H(C$_{18}$H$_{12}$N$_2$)$_n$H: C, 84.35; H, 4.72; N, 10.93. Found: C, 84.27; H, 4.63; N, 10.75.

Figure 3:
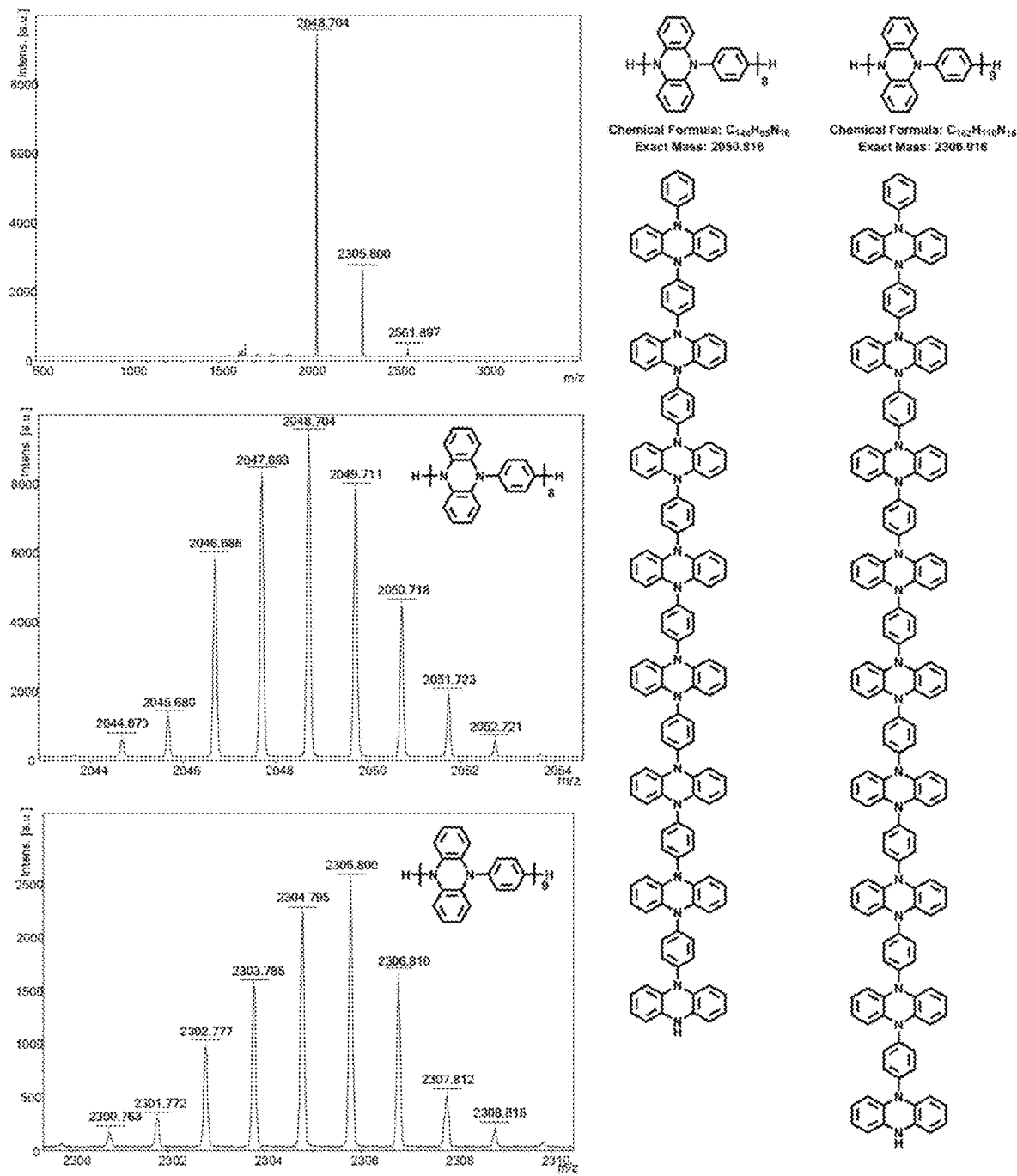
FIG. 3 shows MALDI-TOF Mass spectrum of p-DPPZ.
Figure 4:
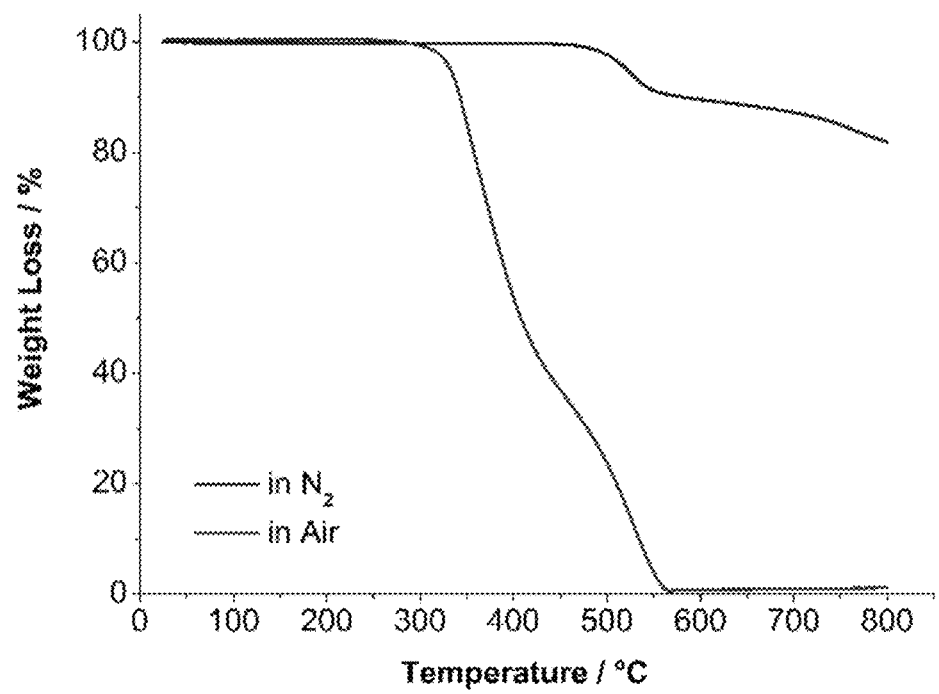
FIG. 4 shows thermogravimetric analysis (TGA) of p-DPPZ in $N_2$ and in air at a heating rate of 10° C./min.
Figure 5:
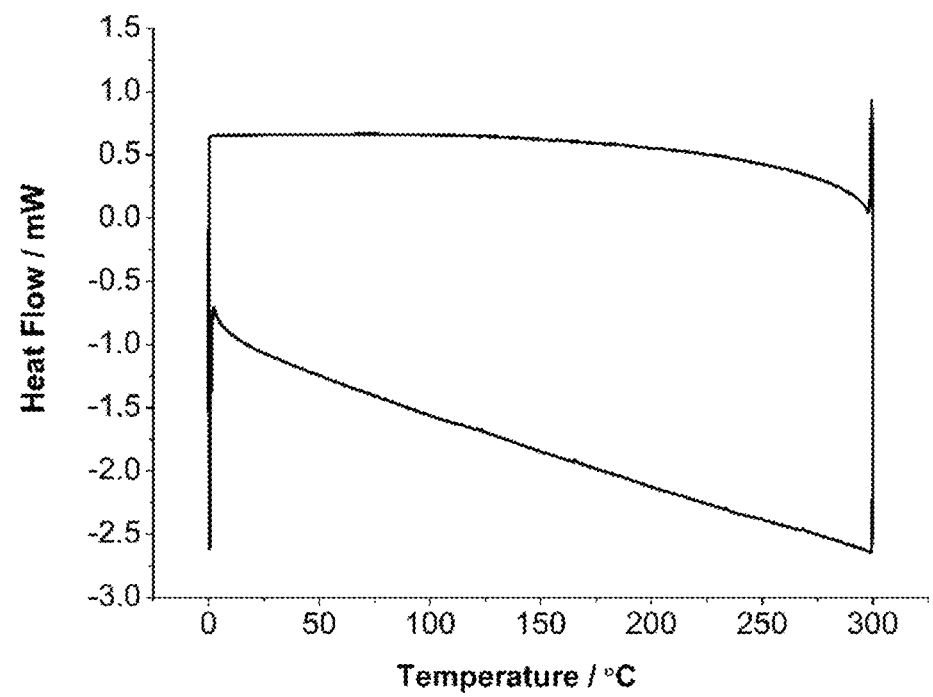
FIG. 5 shows differential scanning calorimeter (DSC) analysis of p-DPPZ in $N_2$ at a heating rate of 10° C./min.
Figure 6:
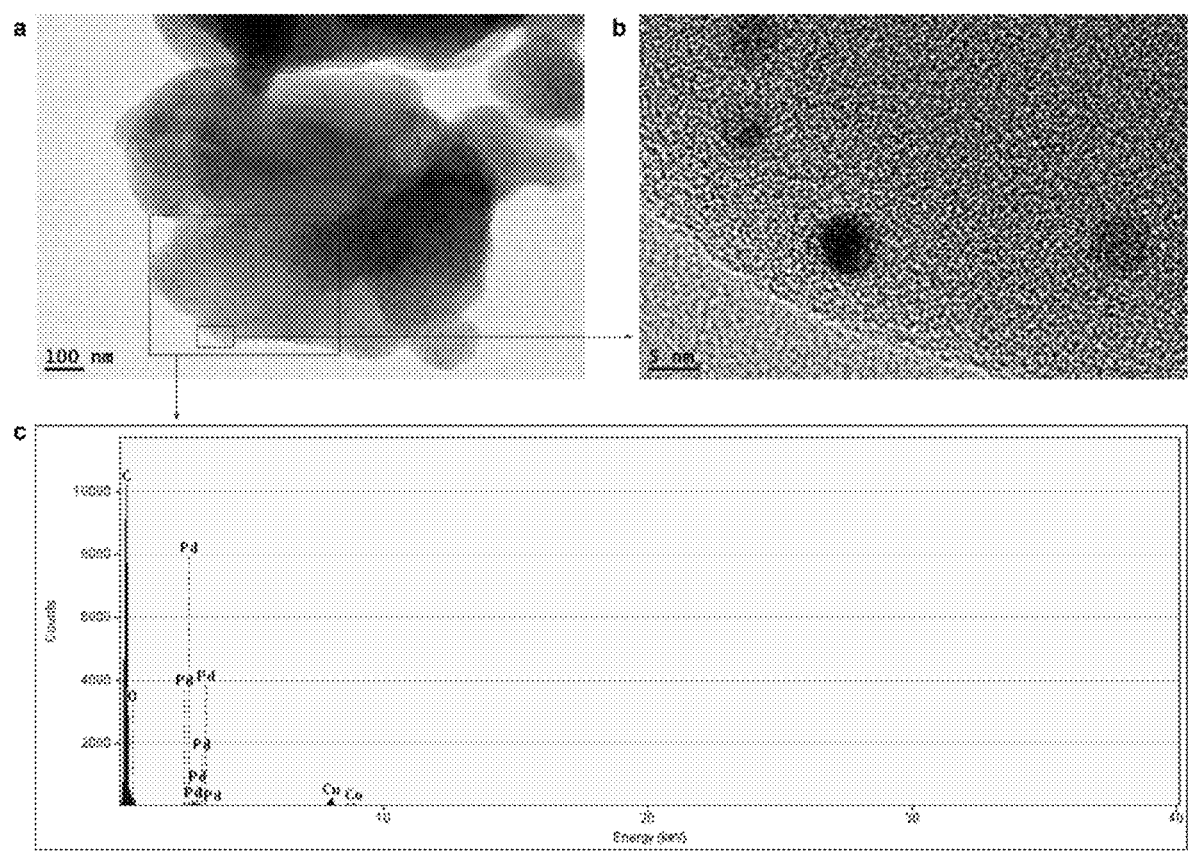
FIGS. 6a and 6b show high-resolution transmission electron microscopy (HRTEM) images of representative p-DPPZ particles and FIG. 6c shows corresponding energy dispersive X-ray spectroscopy (EDX) analysis.

The as-synthesized p-DPPZ typically is composed of 8-9 repeating units (see FIG. 3), which are insoluble in most organic solvents and electrolytes. The p-DPPZ showed good thermal stability with decomposition temperature at 470° C. in N$_2$ and 380° C. in air. And no obvious glass transition or melting in the temperature range of 0-300° C. confirmed by thermogravimetric analysis (TGA) and differential scanning calorimetry (DSC), respectively (see FIG. 4 and FIG. 5). The complete combusted p-DPPZ in air showed a weight loss ≥99.5%. High-resolution transmission electron microscopy (HRTEM) observation indicated that the p-DPPZ is composed of particles with average diameter of 400-800 nm. Corresponding Energy Dispersive X-Ray Spectroscopy (EDX) analysis revealed that traces of Pd nanoparticles in the diameter of 5-10 nm are found to distribute uniformly on the p-DPPZ particles (see FIG. 6). Pd particles should come from the Pd(OAc)$_2$ catalyst during the polymerization, and the weight fraction is less than 0.5% according to the TGA analysis.

Electrode Preparation and Cell Assembly

The electrode was prepared by mixing the as-prepared p-DPPZ, Super P carbon (Timcal Graphite & Carbon), and polyvinylidene fluoride binder (Fisher Scientific) with a weight ratio of 75:15:10 in N-methyl-2-pyrrolidone (anhydrous, Fisher Scientific). The mixture was thoroughly mixed in a Thinky centrifugal mixer (ARE-300) to form the homogenous slurry, which was then casted on an Al foil and dried in vacuum at 115° C. for 12 hrs. The electrode was 10 mm in diameter, and the average mass loading was ca. 2.5 mg·cm$^{-2}$. The cell was assembled with a standard CR2032 coin cell using metallic lithium as the anode, Celgard 2500 as the separator, and 1M LiPF6 in ethylene carbonate/diethyl carbonate (1:1, v: v, BASF Corp.) as the electrolyte.

Results of electro-chemical test of the above prepared cell

Figure 7:
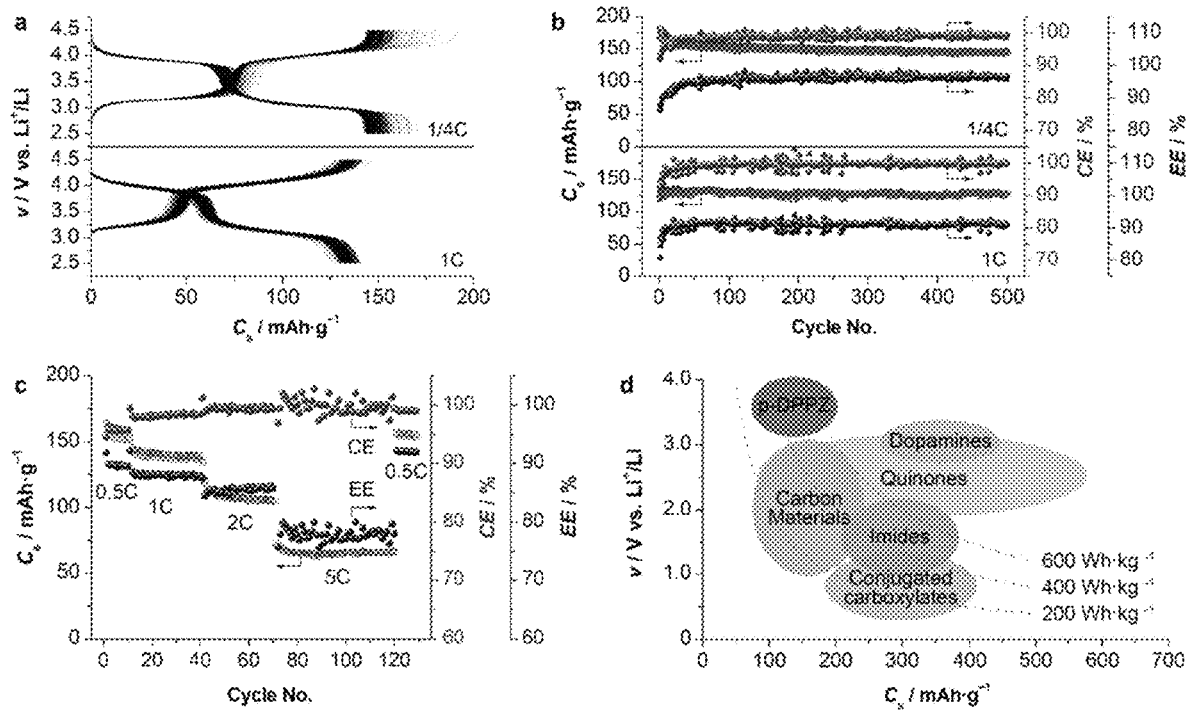

Each of the upper and lower panel of FIG. 7a shows a total 500 charge/discharge cycles of the p-DPPZ|Li cell with current rate of 1/4 and 1 C (1 C corresponds to 209 mA·g$^{-1}$), respectively.

The charge/discharge profiles showed two distinct plateaus locating at the voltage range between 3.8-4.1 and 2.9-3.3 V (vs. Li+/Li), corresponding well to the redox potentials of DPPZ.

The charge/discharge profiles showed good consistency and small voltage hysteresis. The slightly increased omic polarization at 1 C was ca. 100 mV, which is possibly resulted from the more serious Li dendrite formation at higher current density after long cycling. The discharge capacity reached ca. 185 and 145 mAh·g$^{-1}$, and eventually stabilized at ca. 150 and 130 mAh·g$^{-1}$ at 1/4 C and 1 C, respectively, as summarized in FIG. 7b.

The corresponding Coulombic efficiency and energy efficiency maintained around 99% and 95% at 1/4 C, and 99.5% and 90% at 1 C, respectively.

By comparing the performance parameters with other known organic materials, it's obvious that p-DPPZ is highly promising as cathode material for Lithium-ion batteries.

The rate capability as shown in FIG. 7c demonstrated that the p-DPPZ electrode was able to deliver an average specific capacity of 150, 140, 110, and 65 mAh·g$^{-1}$ with corresponding current rate of 1/2, 1, 2 and 5 C, respectively. The cell showed good capacity retention at each current rate, and the capacity recovered back to 150 mAh·g$^{-1}$ when current rate decreased from 5 C to 1/2 C. The capacity drop at high current rate might result from the moderate electron transfer rate and the internal resistance of the electrode, of which the conductive carbon only takes 15% of the total electrode weight. Nevertheless, at moderate current rate, 1/2 C for instance, the p-DPPZ was able to deliver a galvanometric energy density of ca. 530 Wh·kg$^{-1}$ based on the weight of p-DPPZ, or ca. 400 Wh·kg$^{-1}$ based on the total weight of the electrode. In regardless of the excellent cyclability and stability of p-DPPZ, energy density alone is comparable to other reported organic cathode materials as indicated in FIG. 7d.

Results of DPPZ Used as Cathode Active Material in a Half-Cell

Figure 8:
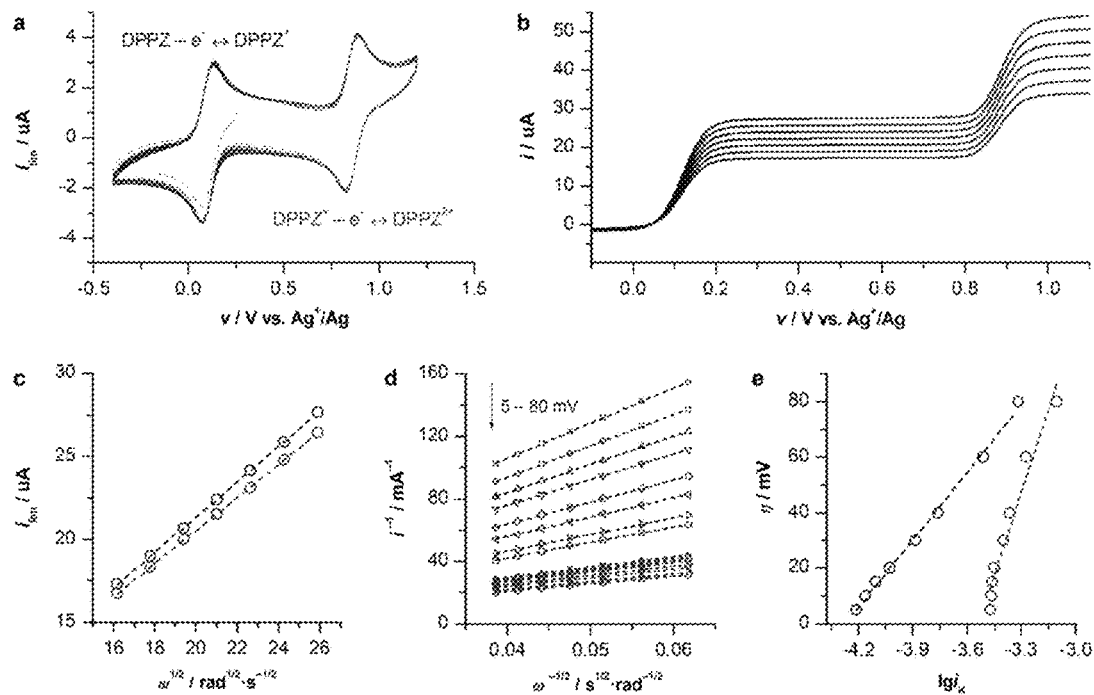
Figure 9:
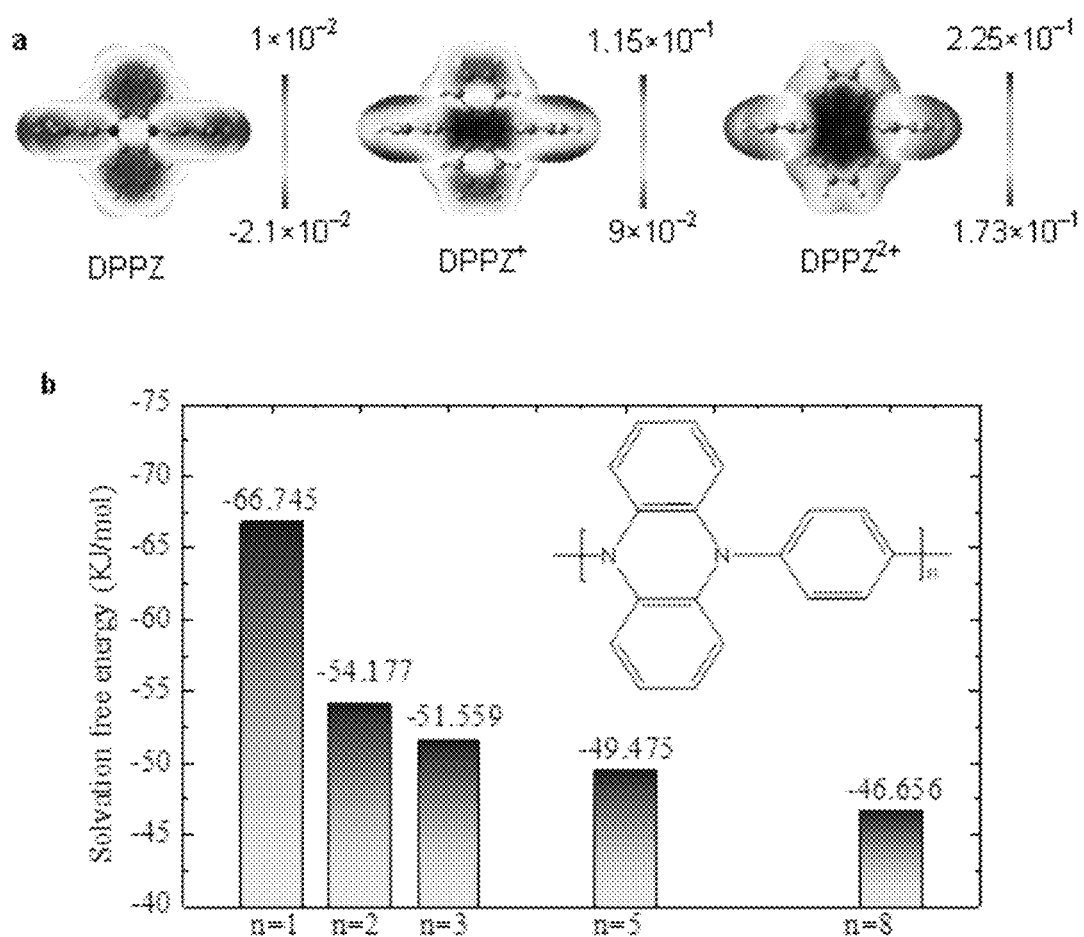
FIG. 9a shows the molecular surface electrostatic potential (ESP) of DPPZ, DPPZ$^+$ and DPPZ$^{2+}$. The charge density around the molecules is calculated using B3lyp level theory and 6-31 g(d,p) basis set using Gaussian 09 package and plot the picture using Gview after geometry optimization.
FIG. 9b shows the calculated solvation free energy of different oligomers with n=1, 2, 3, 5 and 8. The solvation free energy increases with the increasing of n, indicating the decreased solubility in p-DPPZ with higher n.

DPPZ was subjected to half-cell electrochemical measurements at room temperature. FIG. 8a shows the cyclic voltammetry (CV) profiles of a 1.14 mM solution of DPPZ in 1M LiPF6 ethylene carbonate/diethyl carbonate (1:1, v: v) on a glassy carbon electrode. During a repeated potential sweeping for 100 cycles, the CV profiles exhibited two well-defined redox peaks, corresponding to a distinct two-step, single-electron transfer process, and suggesting good reversibility and electrochemical stability. The redox potentials were found to be 0.07 and 0.89 V (vs. Ag$^+$/Ag), which are in consistent of the calculated values. Rotation of this disk at a variety of rates yielded two mass-transport-limited currents (FIG. 8b). The DPPZ and DPPZ$^+$ diffusion coefficient could thus be determined through Levich plots (FIG. 8c) to be 1.5×10$^{-6}$ and 1.3×10$^{-6}$ cm$^2$·s$^{-1}$, respectively. Koutecký-Levich analysis at low overpotentials (FIG. 8d) could be extrapolated to infinite rotation rate to obtain the kinetic current. Plotting the overpotential as a function of the logarithm of kinetic current (FIG. 8e), the x-intercept gave the exchange current, through which the electron transfer rate constant could be calculated to be 7.7×10$^{-3}$ and 4.2×10$^{-2}$ cm·s$^{-1}$ for the redox reaction of DPPZ–e$^-$→DPPZ$^+$ and DPPZ$^+$–e$^-$→DPPZ$^{2+}$, respectively. Both rate constants are comparable with other known organic materials for battery application.

The above results of DPPZ reveals that it can be suitably used as cathode active material.

General Characterization Method.

MALDI-TOF mass spectra were recorded on a Bruker Ultraflextreme instrument. Cyclic voltammetry and differential pulse voltammetry measurements were performed in in 1M LiPF$_6$ ethylene carbonate/diethyl carbonate (1:1, v: v) on a CHI 870D electrochemical analyser with a three-electrode cell. Thermogravimetric analysis (TGA) and Differential scanning calorimeter (DSC) measurements were carried out on a METTLER TA instrument at a heating rate of 10° C. min$^{-1}$ under nitrogen or air flow. High-resolution transmission electron microscopy (HRTEM) images were measured by transmission electron microscope (TEM, FEI Tecnai G2F20). XRD pattern of the powder was measured on a Panalytical X-ray diffractometer. Copper Kα line was used as a radiation source with λ=1.5418 Å.

RDE Study.

The diffusion coefficient of DPPZ and DPPZ$^+$ is determined from Levich plot, $i_{lim}$=0.620nFAD$^{2/3}$ω$^{1/2}$ν$^{-1/6}$ C, where $i_{lim}$ is the limiting current, n is the number of electrons in the charge-transfer step, F is Faraday constant (96485 C·mol$^{-1}$), A is the area of the rotating disk (0.0707 cm$^2$), D is the diffusion coefficient of DPPZ or DPPZ$^+$, co is the rotation speed, v is the kinematic viscosity of the ethylene carbonate/diethyl carbonate electrolyte (4×10$^{-2}$ cm$^2$·s$^{-1}$), and C is the prepared bulk concentration of DPPZ (1.1×10$^{-6}$ mol·cm$^{-3}$). The diffusion coefficient of DPPZ and DPPZ$^+$ is calculated to be ca. 1.5×10$^{-6}$ and 1.3×10$^{-6}$ cm$^2$·s$^{-1}$, respectively. The reciprocal of the current at overpotentials of 5, 10, 15, 20, 30, 40, 60 and 80 mV is plotted versus the reciprocal of the square root of the rotation rate. The data for each potential are fitted with a straight line; the intercept gives the reciprocal of kinetic current, $i_K$, the current in the absence of mass transport limitations (the extrapolation to infinite rotation rate). The x-intercept gives the exchange current, i0, in the plot of η as a function of lg$i_K$. The exchange current is equal to nFk$_0$C, where k$_0$ is the electron transfer rate constant of DPPZ or DPPZ$^+$. The electron transfer rate constant is calculated to be 7.7×10$^{-3}$ and 4.2×10$^{-2}$ cm·s$^{-1}$ for the redox reaction of DPPZ–e$^-$→DPPZ$^+$ and DPPZ$^+$–e$^-$→DPPZ$^{2+}$, respectively.

Electron Configuration Simulation.

Electron configurations of all the molecules were calculated by DFT method within the framework of the Gaussian 09 package. The standard Pople basis set, 6-31G++(d,p), combined with the Lee-Yang-Parr exchange correlation functional (B3LYP) was used for all calculations. For each molecule, the geometry was fully optimized to achieve the lowest total energy before energy level calculation, and all possible spin multiplicities were explored (S=0, 1, 2), among which we chose the one with the lowest energy for comparison between different molecules.

EC/DEC are used as the solvents within the SMD. Static dielectric constant (ε=89.6(EC)×0.5+2.84(DEC)×0.5=46.22) is set for these two solvents configuration. The rest of the solvent parameters are based on a solvent having similar dielectric constant as EC:DEC=1:1 (ε=37.781, N,N-dimethylacetamide). The thermal correction to Gibbs free energy is obtained from vibrational frequency calculations in the solvent model. No negative frequency is found in any of the optimized structures. The redox potential of DPPZ is calculated using the formula E0=(G$_f^0$–G$_i^0$)/nF–C, where G$_f^0$ and G$_i^0$ are the sum of electronic and thermal Gibbs free energy of the final and initial states of the organic molecule, n is the number of electrons in the redox process, and F is the Faraday constant (23.061 Kcal·V$^{-1}$·mol$^{-1}$). C is a constant, which is relevant to the reference electrode. The calculated redox potential of this molecule is 0.97 V and –0.04 V (vs. Ag$^+$/Ag), corresponding to the reactions of DPPZ–e$^-$→DPPZ$^+$ and DPPZ$^+$–e$^-$→DPPZ$^{2+}$, respectively. According to the DFT calculation, there's more obvious uneven charge density around DPPZ$^+$/DPPZ$^{2+}$ molecule compared with DPPZ. The carbonate based solvent molecules tend to interact with the polar cationic moiety of DPPZ$^+$/DPPZ$^{2+}$ due to the presence of polarizable oxygen atoms that are slightly negatively charged. Hence, the solvent molecules will have preferential positions within the solvation sphere based on the charge density distribution of the DPPZ$^+$/DPPZ$^{2+}$ molecule, resulting in the dissolution of DPPZ$^+$/DPPZ$^{2+}$. The dissolution causes serious shuttle effect to prevent the cell from stable cycling. To eliminate the shuttle effect, a practical way is to polymerize DPPZ into polymer/oligomer as have been achieved in the present invention.

The invention claimed is:

1. An oligomer of the following formula (I):

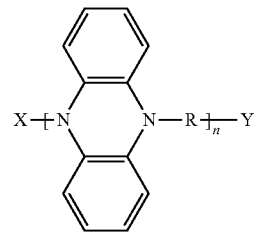

Formula (I)

wherein X is H or phenyl; Y is H,

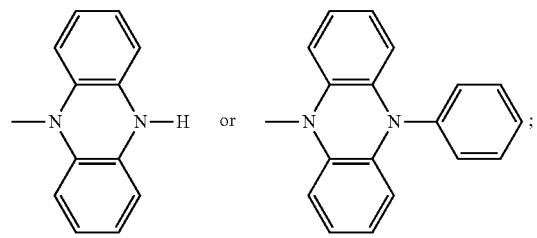 [SMILES: CN1c2ccccc2Nc2ccccc21 ; CN1c2ccccc2N(c2ccccc2)c2ccccc21]

R is p-phenylene; and n is from 8 and/or 9.

2. A cathode active material, comprising the oligomer of the formula (I) according to claim 1.

3. A battery, comprising the oligomer of the formula (I) according to claim 1.

\* \* \* \* \*